United States Patent [19]
Kovalic et al.

[11] Patent Number: 5,569,202
[45] Date of Patent: Oct. 29, 1996

[54] CATHETER NEEDLE TIP PROTECTOR

[75] Inventors: Gerald J. Kovalic, Odessa, Fla.;
Joseph J. Chang, Avon, Conn.

[73] Assignee: Johnson & Johnson Medical, Inc., Arlington, Tex.

[21] Appl. No.: 482,592

[22] Filed: Jun. 7, 1995

[51] Int. Cl.⁶ ..................................................... A61M 5/00
[52] U.S. Cl. ........................ 604/110; 604/192; 604/198; 604/263
[58] Field of Search ............................... 604/192–198, 604/110, 263, 239–243

[56] References Cited

U.S. PATENT DOCUMENTS

| | | |
|---|---|---|
| 4,631,057 | 12/1986 | Mitchell . |
| 4,725,267 | 2/1988 | Vaillancourt . |
| 4,944,725 | 7/1990 | McDonald . |
| 4,978,343 | 12/1990 | Dysarz et al. . |
| 5,092,851 | 3/1992 | Ragner . |
| 5,104,378 | 4/1992 | Haber et al. . |
| 5,129,884 | 7/1992 | Dysarz . |
| 5,246,427 | 9/1993 | Sturman et al. . |

Primary Examiner—Randall L. Green
Assistant Examiner—Perry E. Van Over
Attorney, Agent, or Firm—Joseph F. Shirtz

[57] ABSTRACT

A catheter needle tip protector which assures that the needle is secured against accidental punctures after it is withdrawn from a patient's body. A catheter comprises a catheter hub, and a needle tip protector positioned within the catheter hub. A catheter needle defines a needle tip, with the needle being secured to a needle housing by first and second unequal biasing wires which extend between the needle housing and the needle tip protector. When the needle is withdrawn from the catheter hub, the first and second biasing wires extend the needle tip protector relative to the needle to an oblique position caused by the unequal biasing in which the needle tip is positioned within the needle tip protector. The first and second unequal biasing wires can comprise first and second coiled wires, which can have different biasing strengths to bias the needle tip protector to the oblique position, or can have different lengths to bias the needle tip protector to the oblique position. In one embodiment, the first and second coiled wires are encased within a sleeve in a bellows-like structure.

5 Claims, 1 Drawing Sheet

CATHETER NEEDLE TIP PROTECTOR

BACKGROUND OF THE INVENTION

1. Field of the Invention

The present invention relates generally to an intravenous (IV) catheter needle tip protector, and more particularly pertains to an IV catheter needle tip protector which provides a safety mechanism which offers clinical personnel fail-safe protection against accidental punctures by a used IV needle by automatically protecting the pointed tip of the needle after it is withdrawn from the body of a patient.

2. Discussion of the Prior Art

The present invention relates to clinical apparatus of the type in which pointed needles are used to puncture the skin of a patient, and in particular to catheters employing such needles to effectuate venous punctures.

It is well known and common practice by physicians to inject fluids and drugs directly into the bloodstream of patients. Also, during surgical operations, it is frequently necessary to administer whole blood transfusions and parenteral fluids. Historically, introduction of such fluids into the cardiovascular system of a patient has required the making of a venipuncture using a hollow rigid needle having a proximal attachment site for fluid connecting the needle to a source of intravenous fluid or the like. This method of administering fluids created some persisting problems in the art. Primarily, the rigidity of the needle within the vein requires that the needle, usually on the arm, be maintained, for reasons of safety, in a fixed position at the general site of the venipuncture throughout the duration of fluid administration or transfusion, which may consume considerable time. Secondly, where it has been necessary to periodically draw blood samples and/or successively administer intravenous fluids, the patients may be required to experience a venipuncture each time, which repeated venipunctures are generally highly traumatic.

More recently it has been the practice to insert a flexible catheter tube into a vein and leave the catheter tube in such a position for purposes such as periodically administering fluids, transfusions and medication, collecting of blood samples, etc. In this way, the trauma, extravasation, infiltration, etc., of repeated venipunctures are avoided and the danger and discomfort of leaving a rigid needle in the body for a prolonged period of time are overcome. To place the distal end of such a flexible catheter tube within a body cavity, such as a vascular cavity, a cannulated or hollow needle is used to make the venipuncture. Thereafter following the venipuncture, the catheter tube, which is telescopically mounted with respect to the needle, is displaced relative to the needle into the vein of the patient. The needle may thereafter be completely removed from the catheter tube and disposed of. Having been in the patient's body, where it may have been exposed to infectious agents, the needle represents an infection hazard to clinical personnel if they should accidentally jab themselves with it after withdrawal.

Intravenous catheters for the infusion of fluids into the peripheral vein of a patient are frequently produced in two general forms: through-the-needle catheters, in which a catheter is threaded through the needle cannula and into the vein of a patient, and over-the-needle catheters, in which the needle and a concentric outer catheter are inserted into the vein, and the needle is then withdrawn from the emplaced catheter.

A typical over-the-needle IV catheter requires the user to remove and then dispose of a contaminated needle after the needle tip and catheter are properly located in the vein of the patient. Once the needle is withdrawn from the catheter, the user's immediate priorities are infusion set connection and site preparation, including the taping of the catheter to the patient. Because of the urgency of these procedures, the needle is normally just dropped conveniently nearby and then retrieved later. Since the needle at this time is exposed and located close to where the user is completing work with the catheter, accidental self-inflicted needle injuries are not uncommon.

The possibility that clinical personnel might contract conditions such as AIDS or hepatitis through accidental punctures by used needles has been regarded seriously. Accordingly, a significant body of prior art has been developed for preventing such accidental punctures.

Unfortunately, almost none of the prior art development has succeeded in producing a device in which the withdrawal of a needle from a patient's body automatically activates a protective mechanism. In each case, it was necessary for the clinical personnel to consciously perform an extra step in order to invoke the protection offered by the prior art., One example is U.S. Pat. No. 4,631,057 to Mitchell which discloses a guard tube capable of sliding forward to protect the pointed end of a hypodermic needle from accidental contact after usage. This mechanism, however, like the rest of the prior art, is only effective if the clinical personnel remember to push the guard tube into its effective position after performing an injection. There is a strong possibility that they will occasionally forget to do this.

Now that the range of conditions to which clinical personnel are exposed as a result of accidental needle punctures includes the condition AIDS, it is even more important to provide a safety mechanism which offers such personnel fail-safe protection, i.e. a device which operates without the need for conscious forethought on their part, a mechanism which automatically protects the pointed end of a needle from accidental punctures after it is withdrawn from the body of a patient.

McDonald U.S. Pat. No. 4,944,725 also addresses this problem, and discloses an intravenous catheter which protects a clinician from accidental puncture which may result in the transfer of dangerous infections. The catheter is introduced with the aid of a needle, which is thereafter withdrawn from the patient's body into a protective housing without exposing the needle during any intermediate stage of the process. The housing is latched in place after needle withdrawal, and for unlocking a catheter hub in place after that time, and withdrawal and locking are effected in one continuous motion.

Vaillancourt U.S. Pat. No. 4,725,267 is also of interest to the present invention by disclosing a post-injection needle sheath for enclosing the pointed end of a needle used with a syringe. The sheath is initially in a compact and secured condition on the needle hub and has a substantial portion of the needle exposed for insertion into a patient or vial. Two embodiments employ a compression spring. Three embodiments have a corrugated portion and a flange portion which are manipulated by a clinician to urge the sheath forwardly to enclose the pointed end of the needle. In all embodiments, the forward end includes a transverse wall in which an aperture is formed which is slightly larger than the diameter of the needle. The exposed needle is protected before usage by a conventionally removable shield which is removed at time of usage. After withdrawal of the needle from the patient, the sheath, with the cap or end portion, is moved forwardly to enclose the sharpened needle. The devices of this patent do not operate automatically to enclose a used needle tip in an obliquely positioned protector similar to the present invention.

SUMMARY OF THE INVENTION

Accordingly, it is a primary object of the present invention to provide an improved catheter needle tip protector.

A further object of the subject invention is the provision of a catheter needle tip protector which automatically functions to assure that the needle is secured against accidental punctures after it is withdrawn from a patient's body.

In accordance with the teachings herein, the present invention provides a catheter having a catheter hub, and a needle tip protector positioned within the catheter hub. A catheter needle defines a needle tip, with the needle being secured to a needle housing by first and second unequal biasing means which extend between the needle housing and the needle tip protector. As the needle is withdrawn from the catheter hub, the first and second biasing means extend the needle tip protector relative to the needle to an oblique position caused by the unequal biasing in which the needle tip is positioned within the needle tip protector.

In greater detail, the first and second unequal biasing means comprise first and second coiled wires, which can have different biasing strengths to bias the needle tip protector to the oblique position, or can have different lengths to bias the needle tip protector to the oblique position. In one embodiment, the first and second coiled wires are encased within a sleeve in a bellows-like structure.

BRIEF DESCRIPTION OF THE DRAWINGS

The foregoing objects and advantages of the present invention for a catheter needle tip protector may be more readily understood by one skilled in the art with reference being had to the following detailed description of several preferred embodiments thereof, taken in conjunction with the accompanying drawings wherein like elements are designated by identical reference numerals throughout the several views, and in which.

DETAILED DESCRIPTION OF THE DRAWINGS

Figure 1:
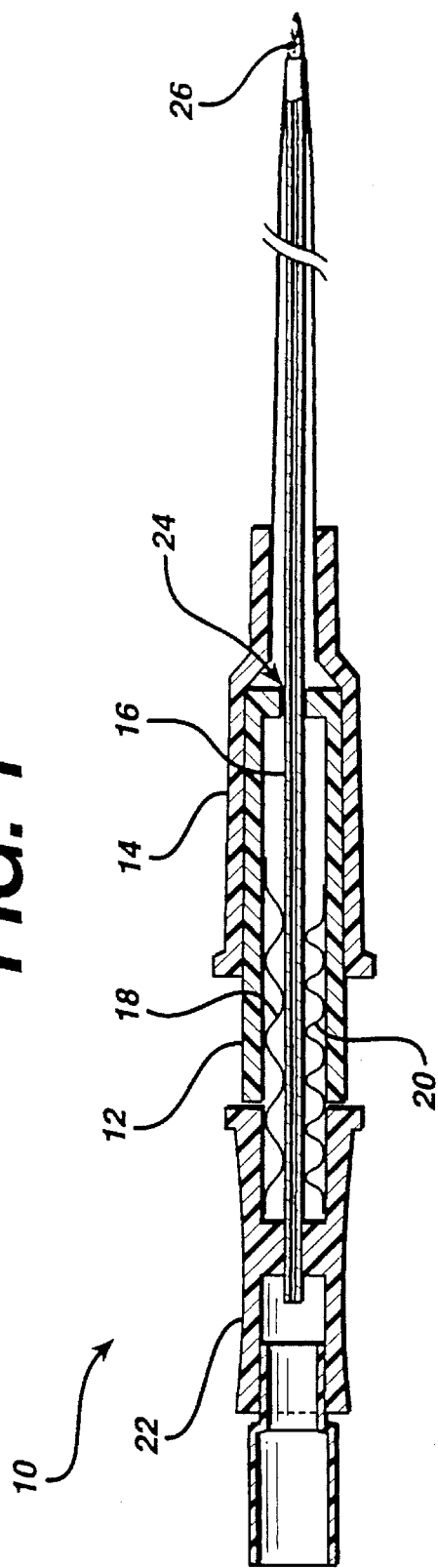
FIG. 1 illustrates an assembled embodiment of an intravenous catheter having a needle tip protector pursuant to the teachings of the present invention positioned within the catheter hub in a retracted position.
Figure 2:
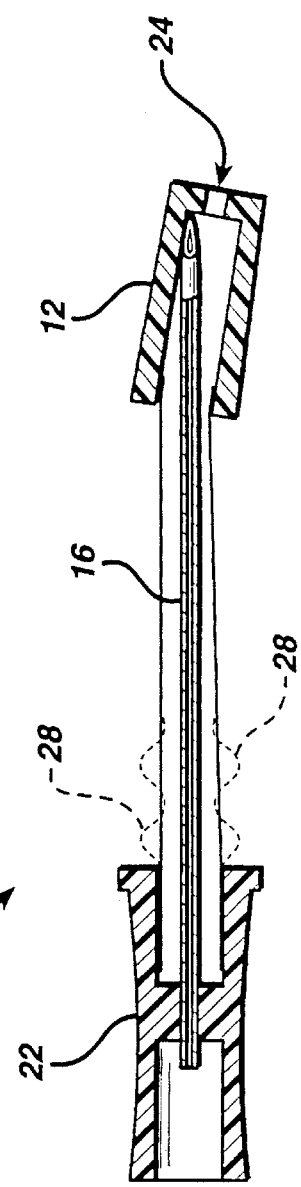
FIG. 2 illustrates the embodiment of Figure 1 after the needle is withdrawn from the catheter hub and the needle tip protector is extended under the bias forces of two coiled wires to an oblique position in which the needle tip is positioned within the protector to prevent accidental contact with the needle tip.

Referring to the drawings in detail, FIG. 1 illustrates an assembled embodiment of an intravenous catheter 10 having a needle tip protector 12 pursuant to the teachings of the present invention positioned within the catheter hub 14 in a retracted position. FIG. 2 illustrates the embodiment of FIG. 1 after the needle 16 is withdrawn from the catheter hub 14, and the needle tip protector 12 is extended under the bias forces of two coiled wires 18, 20 to an oblique position in which the needle tip is positioned within the protector 12 to prevent any accidental contact with the needle 16 tip. The two unequal strength or length coiled wires 18, 20 extend between the needle tip protector 12 and a Plastic Hub Introducer Needle (PHIN) 22. The needle tip protector 12 is preferably formed of a rigid material with a through-hole 24 dimensioned to barely accept the needle 16 diameter.

When the catheter device is threaded, the needle tip protector 12 moves forwardly with the hub 14 until it is positioned beyond the needle tip 26. At this time, the needle tip protector 12 is biasedly or obliquely situated due to the unevenness in biasing strength or length of the two wires 18, 20. This oblique position prevents the needle tip 26 from re-entering the through-hole 24, thus providing needle stick protection. Moreover, the two wire coils 18, 20 can be encased in a sleeve 28, illustrated partially in phantom in FIG. 2, in a bellows-like structure. With this structure, the needle is totally enclosed by the sleeve 12, thus minimizing the possibility of accidental puncture by the used needle.

While several embodiments and variations of the present invention for a catheter needle tip protector are described in detail herein, it should be apparent that the disclosure and teachings of the present invention will suggest many alternative designs to those skilled in the art.

What is claimed is:

1. A catheter comprising:
   a. a catheter hub;
   b. a needle tip protector positioned within the catheter hub; and
   c. a needle having a needle tip, with the needle being secured to a needle housing, and first and second unequal biasing means extending between the needle housing and the needle tip protector, wherein as the needle is withdrawn from the catheter hub, the first and second biasing means extend the needle tip protector relative to the needle to an oblique position caused by the first and second unequal biasing means in which the needle tip is positioned within the needle tip protector.

2. A catheter as claimed in claim 1, wherein the first and second unequal biasing means comprise first and second coiled wires.

3. A catheter as claimed in claim 2, wherein the first and second coiled wires have different biasing strengths to bias the needle tip protector to the oblique position.

4. A catheter as claimed in claim 2, wherein the first and second coiled wires have different lengths to bias the needle tip protector to the oblique position.

5. A catheter as claimed in claim 2, wherein the first and second coiled wires are encased within a sleeve in a bellows-like structure.

* * * * *